United States Patent [19]

Castillo et al.

[11] Patent Number: 5,171,232
[45] Date of Patent: * Dec. 15, 1992

[54] CATHETER HAVING HIGHLY RADIOPAQUE, FLEXIBLE TIP

[75] Inventors: Miguel A. Castillo, Hialeah; Javier E. Castaneda; Eric Glemser, both of Miami, all of Fla.

[73] Assignee: Cordis Corporation, Miami Lakes, Fla.

[ * ] Notice: The portion of the term of this patent subsequent to Sep. 3, 2008 has been disclaimed.

[21] Appl. No.: 729,372

[22] Filed: Jul. 12, 1991

Related U.S. Application Data

[62] Division of Ser. No. 365,477, Jun. 13, 1989, Pat. No. 5,045,072.

[51] Int. Cl.⁵ .............................................. A61M 25/00
[52] U.S. Cl. .................................... 604/280; 128/658
[58] Field of Search ............... 604/264, 280, 281, 282; 128/658

[56] References Cited

U.S. PATENT DOCUMENTS

| | | | |
|---|---|---|---|
| 3,608,555 | 9/1971 | Greyson | 128/658 |
| 3,618,614 | 11/1971 | Flynn | 128/658 |
| 3,749,134 | 7/1973 | Slingluff et al. | 604/280 |
| 4,027,659 | 6/1977 | Slingluff | 128/658 |
| 4,196,731 | 4/1980 | Laurin et al. | 604/280 |
| 4,282,876 | 8/1981 | Flynn | 128/658 |
| 4,283,447 | 8/1981 | Flynn | 128/658 |
| 4,419,095 | 12/1983 | Nebergall et al. | 128/207.15 |
| 4,588,399 | 5/1986 | Nebergall et al. | 128/207.15 |
| 4,657,024 | 4/1987 | Coneys | 128/658 |
| 4,722,344 | 2/1988 | Cambron et al. | 128/658 |
| 4,838,879 | 6/1989 | Tanabe et al. | 128/658 |
| 4,863,442 | 9/1989 | DeMello et al. | 604/282 |
| 4,886,506 | 12/1989 | Lovgren et al. | 128/658 |
| 4,898,591 | 2/1990 | Jang et al. | 604/282 |
| 5,045,072 | 9/1991 | Castillo et al. | 604/280 |

Primary Examiner—Stephen C. Pellegrino
Assistant Examiner—Ralph A. Lewis
Attorney, Agent, or Firm—Gerstman & Ellis, Ltd.

[57] ABSTRACT

A flexible plastic catheter defines a flexible, distal tip. In accordance with this invention, the distal tip comprises a plastic formulation containing sufficient radiopaque agent to be substantially more radiopaque and preferably softer than portions of the catheter proximal to the tip. Thus, the distal tip area of the catheter can be flexible to avoid possible tissue damage as the catheter is advanced, but is still readily visible by x-ray. At the same time, the majority of the catheter may be of normal flexibility and strength.

10 Claims, 1 Drawing Sheet

CATHETER HAVING HIGHLY RADIOPAQUE, FLEXIBLE TIP

This is a division of application Ser. No. 365,477, filed Jun. 13, 1989 now U.S. Pat. No. 5,045,0

BACKGROUND OF THE INVENTION

Several types of catheters are made of a material which is radiopaque, so that the catheter is visible under fluoroscopy or other form of x-ray diagnosis. Typically, catheters for the arteriovenus system are made radiopaque generally by compounding into the plastic material of the catheter a radiopaque filler such as bismuth subcarbonate, bismuth trioxide, or barium sulfate.

Difficulties arise with thin-walled catheters, for example the well-known P.T.C.A. guiding catheters. These catheters are generally thin-walled since they are for the purpose of guiding another device thru its lumen. The lumen must be sufficiently large to allow the injection of contrast media around this second device (typically a PTCA dilatation catheter). As such, these thin walled catheters do not show up well on the fluroscope or other forms of x-ray, even when they are loaded as much as possible with a radiopaque agent. The loading of radiopaque agent has an upper limit which is governed in part by the desired physical characteristics of the catheter. Plastic materials with heavy loadings of radiopaque agent decrease in flexibility, which may limit their use at higher concentrations in many types of catheters.

It is particularly desirable for the distal tip of the catheter to be visible in a fluoroscope or other form of x-ray, so that the positioning of the catheter a its distal end can be precisely determined. In the prior art, this has been accomplished by providing a metal ring to the catheter adjacent the distal end. It is generally undesirable to place the metal ring exactly on the distal tip of the catheter, since the distal tip needs to be very soft and pliable. However, when the metal ring is spaced from the distal tip, as is conventional, it still provides a rigid section of the catheter which can be undesirable. Also, since the metal ring is spaced from the distal tip, the use of such a metal ring does not completely resolve the problem of precisely locating the distal tip of the catheter within the body by means of a fluoroscope during a medical procedure, since the metal ring is and must be spaced from the distal tip.

In accordance with this invention, a catheter is provided which is of the appropriate stiffness throughout, and preferably free from any metal radiomarker member such as a metal ring, yet which carries a distal tip which is considerably softer and more radiopaque than the rest of the catheter. Thus, the catheter may be as stiff as desired, but the highly radiopaque tip of the catheter can be soft to avoid vessel trauma, while providing reliable locatability for the distal end by fluoroscope or the like. At the same time the desired degree of flexibility is provided along every portion of the catheter, including the distal tip and the catheter segment where in the prior art a metal ring is normally carried to achieve locatability.

DESCRIPTION OF THE INVENTION

In this invention, a flexible plastic catheter defines a flexible, distal tip. The distal tip comprises a plastic formulation containing sufficient radiopaque agent to be substantially more radiopaque than portions of the catheter proximal to said tip. This is possible, in part, because the distal tip of the catheter may comprise a resin that is softer than other portions of the catheter, so that it remains softer with higher radiopaque filler loadings. For example, to make the desired radiopaque tip, a typically polyurethane resin having a shore A durometer of 75A to 85A may be loaded with 40 (or 45) to 75 weight percent of radiopaque filler.

Thus, in accordance with this invention, the distal tip may desirably comprise a higher weight percent of radiopaque agent than the plastic formulation of the catheter portions proximal to the tip. As an alternate embodiment, the distal tip may carry a more effective radiopaque agent at generally equal concentrations to the concentration of a less effective radiopaque agent in the remainder of the catheter.

It is preferred for the plastic of the distal tip to comprise 50–70 weight percent of radiopaque agent, preferably bismuth trioxide. In this circumstance, it is generally preferred for the portions of the catheter proximal to said tip to comprise from 25–38 weight percent of radiopaque agent, for example, bismuth trioxide also.

It is generally preferred for the plastic formulation from which the tip is made to comprise polyurethane as a structural binder (i.e. resin) ingredient, for example polyether-polyurethane or polyester-polyurethane. It is preferred for the plastic formulation that makes up the remainder of the catheter to comprise a structural binder ingredient that is sealingly compatible with polyurethane, or if the tip is other than polyurethane, then the structural binder ingredient is preferably sealingly compatible with whatever constitutes the structural binder of the distal tip. Generally, the structural binders of the distal tip and the remainder of the catheter comprise the same, or similar, formulations for the best sealing compatibility; i.e. when the distal tip comprises polyurethane, the remainder of the catheter also comprises polyurethane. Thus, it is possible for the distal tip to be separately formed from the rest of the catheter body, and then to be heat sealed in any appropriate way to the remainder of the catheter body, for example, by heating in an appropriate die, so that the two members bond together.

While it is preferred for both the distal tip and the remainder of the catheter body to comprise polyurethane, other inert plastic materials besides polyurethane may be used to manufacture catheters, for example, polyethylene, poly(ethylene terephthalate) and other polyesters, polypropylene, polyamides such as nylon, elastomers such as latex or Kraton (a product of Shell Chemical Company), or the like.

Accordingly, a flexible, radiopaque catheter may be provided, in which the distal tip has a significantly increased radiopaque characteristic, but at the same time the distal tip preferably exhibits more flexibility, to be nondamaging as it advances through body tissues, for example, the arteriovenous system. Such catheters are manufactured with ease, and are preferably free of any metallic radiomarker member, to obtain advantages as described above.

DESCRIPTION OF SPECIFIC EMBODIMENTS

Figure 1:
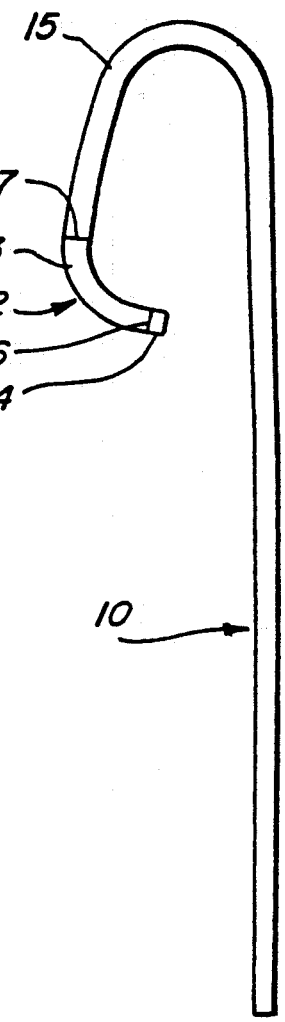
FIG. 1 is a plan view of a P.T.C.A. guiding catheter in accordance with this invention.

Referring to the drawings, P.T.C.A. guiding catheter 10 is shown, having a catheter shaft made in accordance with conventional design for a P.T.C.A. procedure out of a polyether polyurethane formulation. The catheter shown is similar to catheters which have been sold by the Cordis Corporation for P.T.C.A. procedures except as otherwise described herein. The natural shape of the distal end 12 of catheter 10 is as shown in FIG. 1, but catheter 10 is quite flexible so that it can be and is straightened out as it is inserted into the arteriovenous system of the patient. Other designs of catheter ends are also available, and may also incorporate the invention of this application.

Distal end 12 comprises a transition zone 13 which connects distal tip 14 with catheter body 15. Typically, transition zone 13 is free of tubular reinforcing braid, while catheter body 15 carries such reinforcing braid in its interior, in conventional manner.

In accordance with this invention, distal tip 14 is bonded at seal line 16 to the distal end of transition zone 13, which is bonded in similar manner at its other end 17 to catheter body 15. As stated above, this may be accomplished by heating the respective portions while pressed together in a die, so that the polyether polyurethane of the respective sections flows together into intimate contact and forms a firm seal line at junctions 16, 17, while the bore 18 of the catheter remains open.

Distal tip 14 of the catheter is made of a polyether polyurethane formulation which is somewhat different from the polyurethane formulation used to manufacture catheter sections 13 and 15. Specifically, the formulation used to manufacture distal tip 14 may contain 39.7 weight percent of a commercially available polyurethane (Pellethane 80AE, sold by the Dow Chemical Company); 60 weight percent of bismuth trioxide; and 0.3 weight percent of oxidized polyethylene, which is a commercially available and known dispersing agent, release agent, and lubricant for the system.

A specific formulation out of which the catheter body 15 and transition zone 13 may be formulated is as follows: 79.66 weight percent of a commercial polyurethane base similar to the above formulation; 20 weight percent of barium sulfate; and 0.34 weight percent of the above-described oxidized polyethylene ingredient.

While both catheter body 15 and transition zone 13 are flexible, distal tip 14 exhibits greater flexibility and lower Durometer than the rest of the catheter, while it also exhibits substantially greater radiopaque characteristics.

Figure 3:
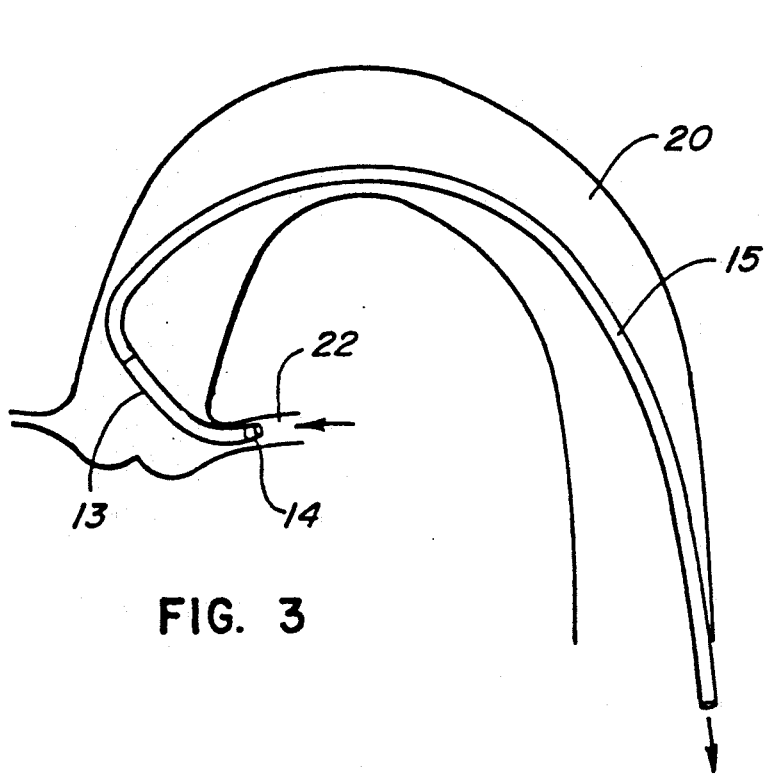
FIG. 3 is a schematic view, similar to a view as might be seen in a fluoroscope during a P.T.C.A. procedure, showing the catheter of this invention passing through the aorta into a coronary artery.
Figure 2:
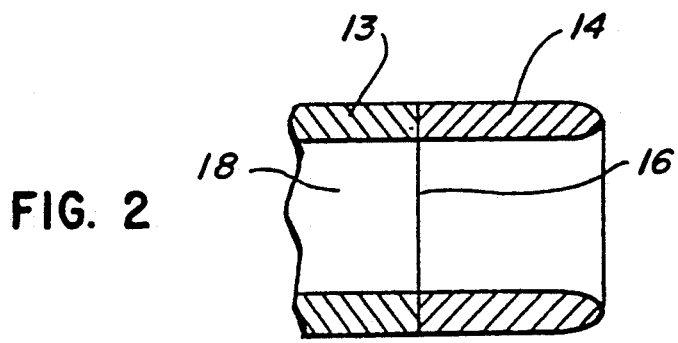
FIG. 2 is a fragmentary, enlarged longitudinal, sectional view of the distal end of the catheter of FIG. 1.

Accordingly, as indicated in FIG. 3, when the catheter of FIG. 1 is inserted into the aorta 20 of a patient, from there curving around so that distal tip 14 occupies a coronary artery 22, distal tip 14 will show up on the fluoroscope with significantly greater intensity than the remainder of catheter 10, to provide the physician who is observing through the fluoroscope or other x-ray means with precise information on the location of the distal tip of catheter 10. This information greatly facilitates the P.T.C.A. procedure, and many other desired medical procedures.

By way of another example, most of catheter 10 may be formulated from 64.86 weight percent of a commercially available polyurethane formulation (Estane 58271-021 of B. F. Goodrich Corporation); 33.5% of bismuth subcarbonate; 1.34% of blue pigment; and 0.33% of a commercially available oxidized polyethylene. The distal tip 14 of such a catheter may be formulated of the following formulation: 49.83 weight percent of the polyurethane formulation described immediately above; 49.83 weight percent of powdered bismuth subcarbonate; and 0.33 weight percent of the oxidized polyethylene. After separate extrusion of the two different formulations into catheter tubes of equal inner and outer diameters, a short segment of the tube formed by the latter formulation may be heat sealed to one end of the tube made from the former formulation, to serve as distal tip 14. X-ray of the catheter shows that the resulting catheter tip exhibited substantially increased radiopaque characteristics.

As a modified formulation of material from which distal tip 14 may be made, the following formulation was prepared: 49.83 weight percent of the polyurethane formulation last described above; 49.83 weight percent of bismuth trioxide; and 0.033 weight percent of the oxidized polyethylene ingredient. This formulation, when formed into distal tip 14 and applied by heat sealing to a polyurethane catheter of the type described above exhibits even greater radiopaque characteristic than that of the previous distal tip formulation.

Additionally, it is generally desirable to use a finely powdered grade of the radiopaque agent, such as bismuth trioxide, bismuth subcarbonate, barium sulfate, or other material, to provide homogeneity to the plastic formulations to which they are added.

The above has been offered for illustrative purposes only, and is not intended to limit the scope of the invention of this application, which is as defined in the claims below.

That which is claimed is:

1. A flexible plastic arteriovenous catheter which defines a radiopaque catheter shaft and flexible distal tip, said distal tip comprising a plastic formulation containing enough radiopaque agent to be substantially more radiopaque than said catheter shaft, said distal tip being softer than said portions of said catheter proximal to said tip.

2. The catheter of claim 1 in which said radiopaque agent is bismuth trioxide.

3. The catheter of claim 1 in which the plastic formulation comprises polyurethane as a structural binder.

4. The catheter of claim 1 which is free of any metallic radiomarker member positioned on or adjacent said distal tip.

5. The catheter of claim 1 in which the plastic of said distal tip comprises essentially 50 to 70 weight percent of radiopaque agent while portions proximal to said distal tip comprises from 25 to 38 weight percent of radiopaque agent.

6. The catheter of claim 1 in which said distal tip portion contains from 25 to 60 weight percent of thermoplastic resin, which resin in unfilled form has a durometer of 75a to 85a, and from 40 to 75 weight percent of a radiopaque filler mixed in said resin, whereby said distal tip portion exhibits improved radiopaque characteristics while remaining soft.

7. A flexible plastic arteriovenous catheter which defines a radiopaque catheter shaft and flexible distal tip, said distal tip comprising a polyurethane formulation containing enough bismuth trioxide radiopaque agent to be substantially more radiopaque than said catheter shaft, said distal tip being softer than portions of said catheter proximal to said tip.

8. The catheter of claim 7 which is free of any metallic radiomarker member positioned on or adjacent said distal tip.

9. The catheter of claim 8 in which said catheter shaft also comprises a polyurethane plastic.

10. The catheter of claim 8 in which said catheter shaft comprises a radiopaque agent dispersed in a flexible plastic.

* * * * *

REEXAMINATION CERTIFICATE (3363rd)

United States Patent [19]
Castillo et al.

[11] B1 5,171,232
[45] Certificate Issued  *Oct. 28, 1997

[54] CATHETER HAVING HIGHLY RADIOPAQUE, FLEXIBLE TIP

[75] Inventors: Miguel A. Castillo, Hialeah; Javier E. Castaneda; Eric Glemser, both of Miami, all of Fla.

[73] Assignee: Cordis Corporation, Miami, Fla.

Reexamination Requests:
No. 90/003,562, Sep. 9, 1994
No. 90/004,079, Dec. 20, 1995

Reexamination Certificate for:
Patent No.: 5,171,232
Issued: Dec. 15, 1992
Appl. No.: 729,372
Filed: Jul. 12, 1991

[*] Notice: The portion of the term of this patent subsequent to Sep. 3, 2008, has been disclaimed.

Related U.S. Application Data

[62] Division of Ser. No. 365,477, Jun. 13, 1989, Pat. No. 5,045,072.

[51] Int. Cl.⁶ ..................................... A61M 25/00
[52] U.S. Cl. ............................... 604/280; 128/658
[58] Field of Search ...................... 128/658; 604/95, 604/96, 100, 101, 280, 281, 282

[56] References Cited

U.S. PATENT DOCUMENTS

4,636,346  1/1987  Gold et al. .......................... 264/139

*Primary Examiner*—Manuel Mendez

[57] ABSTRACT

A flexible plastic catheter defines a flexible, distal tip. In accordance with this invention, the distal tip comprises a plastic formulation containing sufficient radiopaque agent to be substantially more radiopaque and preferably softer than portions of the catheter proximal to the tip. Thus, the distal tip area of the catheter can be flexible to avoid possible tissue damage as the catheter is advanced, but is still readily visible by x-ray. At the same time, the majority of the catheter may be of normal flexibility and strength.

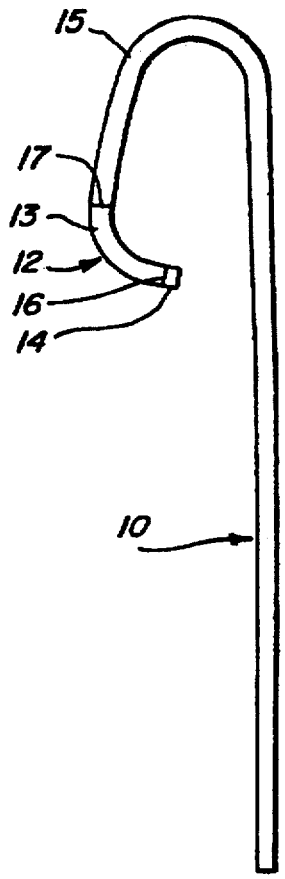

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–10 is confirmed.

* * * * *